United States Patent [19]

Rastelli

[11] Patent Number: 5,256,173
[45] Date of Patent: Oct. 26, 1993

[54] PROCESS FOR REMOVING LIGHT ALCOHOLS FROM GAS STREAMS

[75] Inventor: Henry Rastelli, New Fairfield, Conn.

[73] Assignee: UOP, Des Plaines, Ill.

[21] Appl. No.: 35,144

[22] Filed: Mar. 19, 1993

[51] Int. Cl.$^5$ .................. C07C 29/74; C07C 29/76; C07C 31/04; C07C 31/08

[52] U.S. Cl. .................................... 95/141; 568/917

[58] Field of Search .......................... 568/917; 55/75

[56] References Cited

U.S. PATENT DOCUMENTS

| | | | |
|---|---|---|---|
| 2,882,243 | 4/1959 | Milton | 568/917 |
| 2,985,589 | 5/1961 | Broughton et al. | 568/917 |
| 4,257,885 | 3/1981 | Grose et al. | 568/917 |
| 4,277,635 | 7/1981 | Oulman et al. | 568/917 |
| 4,343,623 | 8/1982 | Kulprathipanja et al. | 568/917 |
| 4,487,614 | 12/1984 | Yon | 568/917 |
| 4,612,405 | 9/1986 | McCaffrey et al. | 568/917 |

*Primary Examiner*—Joseph E. Evans
*Attorney, Agent, or Firm*—Thomas K. McBride; Richard G. Miller

[57] ABSTRACT

The light alcohol component of exhaust gases from such commercial operations as paint spraying booths and printing presses is found to be selectively adsorbed, even under high relative humidity conditions, to a surprisingly high degree using bonded high-silica zeolite agglomerates which have been calcined only once to remove the organic templating agent present in the as-synthesized form of the zeolite. Under certain conditions of alcohol concentration and relative humidity, the capacity of the once-calcined zeolite for alcohol adsorption is nearly twice as great as the same zeolite which has been calcined more than once at temperatures high enough to decompose and remove the organic moieties.

8 Claims, No Drawings

PROCESS FOR REMOVING LIGHT ALCOHOLS FROM GAS STREAMS

FIELD OF THE INVENTION

The present invention relates in general to the removal of volatile organic compounds from gas streams and more particularly to the purification of gas streams by the selective adsorption of light alcohol impurities contained therein using particular forms of bonded high-silica molecular sieve adsorbents.

BACKGROUND OF THE INVENTION

A large number of industrial processes involve the use of volatile organic compounds (frequently referred to as VOC's) whose emission into the atmosphere is objectionable because of environmental pollution or the expense of replacement in the process scheme, or both. In either instance it is becoming increasingly necessary to reduce such emissions in a highly effective manner to meet stringent government requirements or to improve the economics of the process.

Accordingly many methods for emission reductions have been proposed which may involve condensation and recovery of the VOC's in the liquid phase, combustion to environmentally acceptable substances such as $CO_2$ and $H_2O$, preferential adsorption on a porous or microporous material such as activated carbon or zeolitic molecular sieves, or absorption in a hydrophilic fluid such as an oil-in-water emulsion as in the HEC process. Combinations of these techniques are frequently employed.

The chemical and physical properties of the light aliphatic alcohols, i.e., methanol, ethanol, n-propanol and isopropanol, coupled with their generally pleasant odor, make this group of solvents highly preferred in a wide variety of industries. As a solvent, ethanol's use is exceeded only by water, and is a key raw material in the manufacture of drugs, plastics, lacquers, polishes, plasticizers, perfumes and cosmetics. The other light alcohols find similar uses. It is found, however, that the adsorbents typically employed in solvent recovery, i.e., activated carbon, low-silica zeolites, aluminas and silica gels, are not very effective for the adsorption and retention of the light alcohols. This is especially true when the fluid stream being treated contains a relatively high concentration of water which is preferentially adsorbed with respect to the alcohols. To increase the selective adsorption of alcohols under these circumstances it has heretofore been proposed to employ highly siliceous molecular sieves, such as silicalite, which are less hydrophilic than low-silica zeolites and consequently exhibit a greater affinity for the less polar alcohols. These organophilic molecular sieves are ordinarily employed in the form of bonded agglomerates prepared by admixing the molecular sieve, after calcination to remove the organic templating agent present as organic cations or simply occluded in the pores system, with water and an inorganic oxide matrix material such as a clay to form an extrudable mass, and firing the extrudate particles to set the binder and activate the molecular sieve.

SUMMARY OF THE INVENTION

In accordance with the present invention, in the process for selectively adsorbing light aliphatic alcohol from a gas stream by passage at a temperature of from 10° C. to 70° C. through a fixed adsorption bed containing a high-silica microporous synthetic zeolitic molecular sieve substantially free of organic moieties initially present as a consequence of its hydrothermal synthesis, said gas stream containing from about 1 to 10,000 ppm (wt.) of said light aliphatic alcohol and a relative humidity of at least 10 percent at the adsorption temperature, the improvement which comprises employing as the adsorbent a bonded agglomerate of said molecular sieve prepared by calcining at a temperature of from 400° C. to 700° C. a green form of said agglomerate comprising water, an inorganic oxide matrix and said molecular sieve in its as-synthesized form for a sufficient time to set the binder and activate the molecular sieve.

DETAILED DESCRIPTION OF THE INVENTION

The present invention is the surprising discovery that there is a very significant difference in the light alcohol adsorptive capacity of high-silica zeolites which undergo two calcinations instead of a single calcination in the formation of the bonded agglomerates used as adsorbent particles. It is the standard practice in the art routinely to dry and then calcine in air at temperatures in excess of about 500° C. the as-synthesized high-silica zeolitic molecular sieves which are prepared hydrothermally from a reaction mixture containing an organic nitrogen-containing templating agent. The initial calcination is performed to remove the cationic and occluded forms of the templating agent which remain in the pore system after formation of the crystal lattice. In most instances the organic moieties are toxic and whether toxic or not, greatly impede the movement through the pore system of extraneous adsorbate species. When these calcined crystals are formed into shaped agglomerates in an inorganic oxide matrix such as clay, it is essential to fire the green agglomerates to set the binder and harden the agglomerates. In view of the very considerable hydrothermal stability of high-silica zeolites, this second firing is generally perceived as being harmless to the zeolite constituent of the agglomerate. In fact, in the case of VOC's other than the light alcohols, the adsorptive capacity of the twice-calcined adsorbent is observed to decrease by a modest amount, i.e., less than about 10%, compared with the once calcined zeolite. In the case of light alcohols, however, a much more dramatic decrease has now been observed in the twice-calcined adsorbent which can be as much as 50% when the concentration of the alcohol in the gas stream being treated is about 100 ppm, and an even greater decrease occurs at lower alcohol concentration. At 30 ppm concentration, the breakthrough loading of the once-calcined zeolite is double that of the twice-calcined adsorbent. The reason for this considerable difference in performance is not presently known with certainty.

As used herein, the term high-silica microporous zeolitic molecular sieve is intended to denote those crystalline aluminosilicates synthesized using an organic templating agent and in which at least about 90, and preferably at least about 95, percent of the framework tetrahedral oxide units are $SiO_2$ tetrahedra. It will be understood that the molecular sieve has pore diameters large enough to admit the light alcohol species to be selectively adsorbed. These molecular sieves clearly exhibit a hydrophobic adsorptive property as evidenced by the fact that they have an adsorptive capacity for water at 25° C. and 4.6 torr water vapor pressure of less than 10 weight percent. In general there is a direct relationship between an increase in the Si/Al$_2$ molar ratio of the molecular sieve and the increase in the degree of hydrophobicity exhibited. Accordingly it is preferred that the framework Si/Al$_2$ ratio be at least about 38 in order that the water adsorption capacity at 25° C. and 4.6 torr be less than about 6 weight percent. This definition is intended to include the so-called silica polymorphs such as silicalite and TEA-silicate which ideally consist entirely of SiO$_2$ tetrahedral units, but in actual practice contain readily detectable amounts of AlO$_2$ tetrahedra in their as-synthesized form. These high-silica molecular sieves and the method for their synthesis are well known in the art. A comprehensive review article by E. M. Flanigen concerning both high-silica zeolites and silica molecular sieves has been published in "Proc. 5th Int. Conf. Zeolites, Naples, 1980," L.V.C. Rees, ed., Heyden, London, pp. 760–780. Silicalite, a particularly preferred adsorbent, is also described in U.S. Pat. No. 4,061,724. A fluorine modified form, F-silicalite, which is even more hydrophobic than silicalite is described in U.S. Pat. No. 4,073,865. These patent disclosures are incorporated by reference herein.

The term as-synthesized as applied to the molecular sieves employed in the practice of this invention means primarily that the organic templating agent of the crystals recovered from the synthesis reaction mixture has not been thermally destroyed by calcination. The recovered crystals can, however, have been washed to remove occluded or sponged mother liquor and the crystals dried at moderate temperatures, usually in the range of 90° to 315° C. Temperatures below about 315° C. are not fully effective to remove the organic moieties from the pore system of the zeolite.

In forming the molecular sieve crystals into agglomerates the well-known procedures of the prior art are extruded pellets and spherical beads is disclosed in detail in U.S. Pa. No. 2,973,327, issued Feb. 28, 1961, to Mitchell et al. In general the process involves mixing from 5 to 35 parts by weight of a clay with 95 to 65 complementary parts by weight of zeolite crystals and sufficient water to render the clay pliant and plastic and forming the resultant mixture into agglomerates of the desired configuration. The extruded pellets most commonly have a cylindrical cross-section, although a wide variety of cross-sectional shapes have been developed which lessen the diffusional paths for adsorbed substrates and thus improve adsorption rates. A preferred pellet for use in the present process is usually referred to as trilobal because of its somewhat three-leaf clover cross-sectional shape. The agglomerates can also be in the form of beads which can be essentially spherical, or oblate or in other respects less than regular spheres. The exact shape of the agglomerates is not a critical factor. The methods for producing such agglomerates are very well known in the art. In the initial forming stage the pellets are "green" but possess sufficient strength to substantially retain their shape during the subsequent firing, usually at about 650° C., to set the binder and activate the molecular sieve. In the case of the agglomerates of the present invention, the activation involves the removal of both adsorbed water and organic moieties from the molecular sieve pore system. The clays employed can be attapulgite, kaolin, sepolite, polygarskite, kaolinite, plastic ball clays, bentonite, montmorillonite, illite and chlorite. Other inorganic oxide binders include alumina, silica, and the refractory oxides such as those of zirconium, magnesium, calcium and chromium.

The feedstocks treated by the process of this invention are not narrowly critical with respect to composition but must contain from 1 to 10,000 ppm by weight, preferably 10 to 1000 ppm (wt.), of one or a mixture of two or more light aliphatic alcohols, i.e., methanol, ethanol and propanol, have a relative humidity of at least 10 percent up to saturation at the purification process conditions of water vapor, and a carrier gas stream such as air, nitrogen or other relatively non-sorbable gas which is not unduly destructive of the adsorbent mass under the imposed process conditions. The process is particularly useful in treating exhaust air streams from spray paint booths, printing presses, pharmaceuticals production, cosmetic formulation operations and the like.

The invention is illustrated by the following comparisons in which clay-bonded extruded pellets of silicalite were employed to treat moist air streams containing various degrees of relative humidity and ethanol. In some instances the adsorbent pellets were formed from as-synthesized silicalite and in others the silicalite had been calcined to remove the quaternary ammonium templating agent used in the silicalite synthesis before being clay-bonded and again fired.

EXAMPLE 1

(a) The testing apparatus comprises a cylindrical stainless steel fixed adsorption bed having an inside diameter of 158 inch and a length of 18 inches. The feedstock flowing to the adsorption bed was formed by bubbling one portion of an air stream through ethanol in a one-gallon Pope vessel and another portion of the air stream successively through water in a five-gallon Pope vessel and water in a one-gallon Pope vessel. The combined effluent streams from these vessels were combined, when necessary, with a third portion of the air stream to provide a high humidity gas stream containing the desired concentration of ethanol. The volumes of the respective streams served as the principal means of controlling the composition of the feedstock entering the adsorption bed. The temperature of the feedstock was at ambient room temperature. The pressure in the bed was 20.7 psia and the flow rate of feedstock into the bed was about 0.6 ft$^3$/min. The adsorption bed was packed with 20 grams of the adsorbent particles to be tested. The effluent from the adsorption bed was monitored by means of a gas chromatograph. The capacity of the adsorbent at the exit of the stoichiometric point of the mass transfer zone from the bed is taken as the ethanol capacity of the various adsorbent particles involved for purposes of comparison.

(b) Using the apparatus and procedure described in part (a) above, the ethanol capacity was determined for a silicalite adsorbent which had the following characteristics:

Form: Extruded and fired cylindrical pellets 1/16"in diameter ground to 14×30 mesh for testing purposes.

Composition (activated basis): 80 wt. % Silicalite having Si/Al$_2$ molar ratio >200. 20 wt. % Clay binder.

Silicalite Activation: Once at 650° C. in air during pellet formation. The silicalite powder used to make the green pellets had been dried in air at <315° C.

The test feedstock was an air stream having a relative humidity of 70% at 22° C. and containing 69 ppm (wt.) ethanol. The ethanol capacity was found to be 2.2 grams ethanol/100 grams adsorbent.

(c) Using the same procedure, apparatus and adsorbent as in part (a) above, but using a test feedstock having a relative humidity of 70 percent at 22° C. and containing 518 ppm (weight) of ethanol, the adsorbent was found to have an ethanol capacity of 4.3 weight percent.

(d) Using the apparatus and procedure described in part (a) above, the ethanol capacity was determined for a silicalite adsorbent which had the following characteristics:

Form Extruded and fired nominally cylindrical pellets ⅛" in diameter ground to 14×30 mesh for testing purposes. Cross-section was trilobal.

Composition (activated basis): 80 wt. % Silicalite having $Si/Al_2$ molar ratio >200. 20 wt. % Clay binder.

Silicalite Activation: Once at >500° C. in air prior to pellet formation and once in air at 650° C. during pellet formation.

The test feedstock was an air stream having a relative humidity of 70% at 22° C. and containing 77 ppm (wt.) ethanol. The ethanol capacity was found to be 1.2 weight percent.

(e) Using the same procedure, apparatus and adsorbent as in part (d) above, but using a test feedstock having a relative humidity of 70 percent at 22° C. and containing 500 ppm (weight) of ethanol, the adsorbent was found to have an ethanol capacity of 3.9 weight percent.

It is readily apparent from the foregoing data that the high-silica adsorbent which was fired only once after synthesis exhibits an unexpectedly high capacity for light alcohols compared with essentially the same adsorbent which had been subjected to two separate calcinations.

Without wanting to be bound by any particular theory, it appears that the difference in adsorptive capacity for ethanol observed for the once-calcined and twice-calcined silicalite adsorbent is not in large part due to a decrease in the surface area of the zeolite resulting from the second thermal treatment. Both of the adsorbents of part (b) and part (d) were analyzed for oxygen capacity measured at −183° C. and 100 torr oxygen pressure. The once-calcined sample had an equilibrium oxygen capacity of 15.14 weight percent whereas the twice-calcined sample had an oxygen capacity of 14.84, i.e., a decrease of only 2 percent. On the other hand, the same two samples were found to exhibit water capacities, measured at 4.6 torr water vapor pressure and 23° C. of 3.91 weight percent and 2.8 weight percent, respectively, providing evidence that the second calcination treatment of the silicalite decreased its capacity for water vapor by 28.4 percent, thus suggesting that the ability of the adsorbent to bond with hydroxyl groups present in both the water and alcohol adsorbate molecules may be involved.

What is claimed is:

1. In the process for selectively adsorbing light aliphatic alcohol from a gas stream by passage at a temperature of from 10° C. to 70° C. through a fixed adsorption bed containing a high-silica microporous synthetic zeolitic molecular sieve substantially free of organic moieties initially present as a consequence of its hydrothermal synthesis, said gas stream containing from about 1 to 10,000 ppm (wt.) of said light aliphatic alcohol and a relative humidity of at least 10 percent at the adsorption temperature, the improvement which comprises employing as the adsorbent a bonded agglomerate of said molecular sieve prepared by calcining at a temperature of from 400° C. to 700° C. a green form of said agglomerate comprising water, an inorganic oxide matrix and said molecular sieve in its as-synthesized form for a sufficient time to set the binder and activate the molecular sieve.

2. Process according to claim 1 wherein the gas stream being treated contains from about 10 to about 1000 ppm (wt.) of light aliphatic alcohol.

3. Process according to claim 2 wherein the gas stream comprises air, light aliphatic alcohol and water vapor.

4. Process according to claim 1 wherein the microporous zeolitic molecular sieve has a water adsorption capacity at 25° C. and 4.6 torr water vapor pressure of less than about 6 weight percent.

5. Process according to claim 4 wherein the molecular sieve has the crystal structure of silicalite.

6. Process according to claim 3 wherein the light aliphatic alcohol comprises ethanol.

7. Process according to claim 3 wherein the light aliphatic alcohol comprises methanol.

8. Process according to claim 3 wherein the light aliphatic alcohol comprises propanol.

* * * * *